(12) United States Patent
DeHeer et al.

(10) Patent No.: US 9,375,342 B2
(45) Date of Patent: Jun. 28, 2016

(54) ADJUSTABLE-SLIDER, EQUINUS BRACE WITH TOE WEDGE

(71) Applicants: Patrick DeHeer, Carmel, IN (US); John H. Moorin, Carmel, IN (US); Ricky Heath, Fishers, IN (US)

(72) Inventors: Patrick DeHeer, Carmel, IN (US); John H. Moorin, Carmel, IN (US); Ricky Heath, Fishers, IN (US)

(73) Assignee: IQMED LLC, Carmel, IN (US)

( * ) Notice: Subject to any disclaimer, the term of this patent is extended or adjusted under 35 U.S.C. 154(b) by 0 days.

(21) Appl. No.: 14/469,545

(22) Filed: Aug. 26, 2014

(65) Prior Publication Data

US 2014/0371648 A1    Dec. 18, 2014

Related U.S. Application Data

(63) Continuation-in-part of application No. 13/439,449, filed on Apr. 4, 2012, now Pat. No. 8,814,815.

(60) Provisional application No. 61/471,302, filed on Apr. 4, 2011, provisional application No. 61/489,398, filed on May 24, 2011, provisional application No. 61/583,474, filed on Jan. 5, 2012.

(51) Int. Cl.
*A61F 5/00* (2006.01)
*A61F 5/01* (2006.01)

(52) U.S. Cl.
CPC ............. *A61F 5/0127* (2013.01); *A61F 5/0125* (2013.01); *A61F 5/0102* (2013.01); *A61F 2005/016* (2013.01)

(58) Field of Classification Search
CPC ............ A61F 2005/016; A61F 5/0102; A61F 5/0125; A61F 5/0127; A61F 2002/5006; A61F 2002/745; A61F 2002/748; A61F 2/68; A61F 2002/5007; A61F 2002/5018; A61F 2002/5033; A61F 2002/5039; A61F 2002/741; A61F 2002/7635; A61F 2/605; A61F 5/0111; A61F 5/0123; A61F 2005/0169; A61F 2/64; A61F 5/0195; A61F 2005/0139; A61F 5/0585; A61F 2002/4205; A61F 2002/4207; A63B 2023/006; A63B 23/0233; A63B 21/0552; A63B 21/0557; A63B 2208/0204; A63B 21/00061; A63B 21/00072; A63B 21/0421; A63B 21/1492; A63B 2208/02; A63B 2225/09; A63B 22/203; A63B 23/00
USPC ...................................... 602/23–28; 128/882
See application file for complete search history.

(56) References Cited

U.S. PATENT DOCUMENTS

| 5,393 A | 12/1847 | Chamberlain |
|---|---|---|
| 73,768 A | 1/1868 | Allen |

(Continued)

FOREIGN PATENT DOCUMENTS

| DE | 102008052369 | 10/2008 |
|---|---|---|
| DE | 102008052517 | 7/2010 |

OTHER PUBLICATIONS

J.A. Radford, et al. "Does stretching increase ankle dorsiflexion range of motion? A systematic review." Br J Sports Med, Aug. 22, 2006, pp. 870-875, 40.

(Continued)

*Primary Examiner* — Michael Brown
(74) *Attorney, Agent, or Firm* — D'Hue Law LLC; Cedric A. D'Hue

(57) ABSTRACT

Devices and processes used to treat ankle equinus. More specifically, the present disclosure relates to a brace and the corresponding method of use to treat equinus by stretching the Gastrocnemius muscle.

16 Claims, 11 Drawing Sheets

(56) References Cited

U.S. PATENT DOCUMENTS

| | | | |
|---|---|---|---|
| 265,942 A | 10/1882 | Burns | |
| 2,413,634 A * | 12/1946 | Kolarik | 602/16 |
| 2,516,872 A | 8/1950 | Hauser et al. | |
| 2,827,897 A | 3/1958 | Pawlowski | |
| 2,943,622 A | 7/1960 | Nelson | |
| 3,958,567 A | 5/1976 | Callender, Jr. | |
| 4,632,096 A | 12/1986 | Harris | |
| 4,848,326 A | 7/1989 | Lonardo | |
| 4,981,132 A | 1/1991 | Chong | |
| 5,224,925 A | 7/1993 | Varn | |
| 5,378,223 A | 1/1995 | Grim et al. | |
| 5,490,831 A | 2/1996 | Myers et al. | |
| 5,891,071 A | 4/1999 | Stearns et al. | |
| 5,891,077 A | 4/1999 | Gilman et al. | |
| 6,024,713 A | 2/2000 | Barney | |
| 6,048,326 A | 4/2000 | Davis et al. | |
| 6,096,942 A | 8/2000 | Hack | |
| 6,171,272 B1 * | 1/2001 | Akita et al. | 602/28 |
| 6,280,404 B1 | 8/2001 | Morinaka et al. | |
| 7,077,818 B2 | 7/2006 | Ingimundarson et al. | |
| 7,462,159 B1 | 12/2008 | Shlomovitz et al. | |
| 7,462,160 B2 * | 12/2008 | Nobbe et al. | 602/27 |
| 8,777,884 B2 | 7/2014 | DeHeer et al. | |
| 2004/0002672 A1 | 1/2004 | Carlson | |
| 2009/0069732 A1 | 3/2009 | Jackovitch | |
| 2010/0069807 A1 | 3/2010 | Cox | |
| 2012/0253253 A1 | 10/2012 | DeHeer et al. | |
| 2012/0283613 A1 | 11/2012 | DeHeer et al. | |
| 2013/0247421 A1 | 9/2013 | Santos | |

OTHER PUBLICATIONS

Office Action, U.S. Appl. No. 13/439,449, Oct. 22, 2013. 7 pages.
Gallagher, Douglas G. Amendment Response to Office Action of Oct. 22, 2013, U.S. Appl. No. 13/439,449, Feb. 21, 2014. 17 pages.
Notice of Allowability and Fee(s) Due, U.S. Appl. No. 13/439,449, Apr. 25, 2014. 5 pages.
Notice of Allowability and Fee(s) Due, U.S. Appl. No. 13/480,430, Mar. 3, 2014. 5 pages.

* cited by examiner

ADJUSTABLE-SLIDER, EQUINUS BRACE WITH TOE WEDGE

REFERENCE TO RELATED APPLICATIONS

The present application is a continuation-in-part of U.S. Non-provisional patent application Ser. No. 13/439,449, filed Apr. 4, 2012, which claims the benefit of: U.S. Provisional Patent Application Ser. No. 61/471,302, which was filed Apr. 4, 2011; U.S. Provisional Patent Application Ser. No. 61/489,398, which was filed May 24, 2011; and U.S. Provisional Patent Application Ser. No. 61/583,474, which was filed Jan. 5, 2012, the disclosures of which are expressly incorporated by reference.

FIELD

The present disclosure relates to devices and processes used to treat ankle equinus. More specifically, the present disclosure relates to braces or device and their methods of use to treat equinus by stretching the Gastrocnemius muscle and/or the Soleus muscle.

BACKGROUND

Equinus is typically described as a condition in which the upward bending motion of the ankle is limited. Equinus is defined as the inability or lack of ankle joint dorsiflexion less than a right angle relative to the leg.

Equinus may result in a lack of flexibility past the right angle relative to the leg. Referring to FIGS. 1-3, someone suffering with equinus may lack the flexibility to bring the top of foot 18 past a right angle)(90°) relative to the leg and toward the front of the leg. A typical maximum ankle range of motion for dorsiflexion is indicated as twenty-five degrees) (25°) less than a right angle relative to the leg. Equinus may also be characterized as a limited ankle range of motion for dorsiflexion which is no more than five (5°), ten(10°) or even fifteen degrees (15°) less than a right angle relative to the leg.

There are several possible causes for limited range of ankle motion. Limited range of ankle motion is often due to tightness in the calf muscles (the soleus muscle and/or the gastrocnemius muscle). Shortening of the gastrocnemius muscle (also known as gastroc equinus) is a very common condition which may affect most people because the gastrocnemius muscle crosses two joints. Gastrocnemius muscle 24 originates above knee 12 joint, while soleus 26 originates below knee 12 joint. Both muscles join to form the Achilles tendon, which attaches to the heel. Therefore, the gastrocnemius muscle crosses two joints: knee 12 and ankle 16, while soleus muscle 26 only crosses ankle 16 joint.

Regardless of the cause of limited ankle motion, someone suffering with equinus can develop a wide range of foot problems. There are several ways to treat limited ankle range of motion, such as gastroc equinus, including stretching exercises, orthotics with heel lifts, padding, molded shoes, serial casting, as well as night splints and braces.

Many current night splints allow user 22 to sleep with their knees bent. Current night splints and braces do not lock knee 12 into extension as they do not extend above knee 12. Failure to lock knee 12 into extension means that a person experiencing gastroc equinus does not stretch gastrocnemius muscle 24, and therefore is only stretching soleus muscle 26.

Many current night splints and braces are awkward and uncomfortable for sleeping. Since night splints and many current braces are supposed to be worn throughout the night, an awkward or cumbersome night splint or brace may cause user 22 to either not get a good night's sleep or cause user 22 to remove the device. If user 22 does not get a good night's sleep, user 22 may not choose to use the device in the future. This lack of compliance leads to the current devices not performing their intended function.

Even if knee 12 is kept completely straight by user 22, the night splint or brace is not the reason for a complete stretch of gastrocnemius muscle, because there is no above the knee extension locking the knee joint.

If the night splint or brace does not lock knee 12 in full extension while dorsiflexing ankle 16 joint, the device is not providing the preferred method of treatment.

Both U.S. Pat. No. 8,777,884 (DeHeer, et al.) and U.S. Patent Publication No. 2012/0253253 A1 (DeHeer, et al.), describe a hinged equinus brace device constructed with a footplate and a plurality of adjustable elongated rods (lateral and medial) to run along lateral and medial portions of the leg which extend above the knee of the user to the foot of the user for placement into the device. Although these devices seek to lock the knee in full extension while dorsiflexing the ankle joint, residual bending at the back of the knee joint from shifting of the leg while in the device may prevent complete and optimal positional extension and dorsiflexion. Additionally, excess tools are required to install the device on a user's leg. Multiple parts also can be burdensome to manufacture or repair and, in effect, be cost prohibitive.

Therefore, a need remains for a brace that locks the knee in full extension while dorsiflexing the ankle joint.

SUMMARY

The present disclosure includes a device for treating ankle equinus by stretching the Gastrocnemius muscle and soleus muscle, the device comprising: a brace comprising an elongated rod, an adjustable slider, a clamp and a footplate, wherein the elongated rod includes a left sidewall and a right sidewall configured to attach to the footplate, and a plurality of side webbing slots, wherein the left and right sidewalls each include at least one tab for fixing an angle of dorsiflexion for an ankle of a user; wherein the footplate includes a bottom plate, a left side plate and a right side plate with each side plate having at least one opening for attachment to the at least one tab of the left and right sidewalls of the elongated rod through the side plates, an ankle hinge, and a plurality of foot webbing slots; wherein the ankle hinge of the elongated rod and the foot plate creates an opening for the heel of a user; the adjustable slider configured to be attached adjacent to the elongated rod above the heel, the adjustable slider defining a center slot extending along a substantial length of the slider, wherein the adjustable slider extends vertically to change the overall length of the device to accommodate different leg lengths of different users; and the clamp configured for connecting the adjustable slider and the elongated rod; and a wedge supported by the footplate, wherein the brace locks the knee in extension while also locking the ankle of a user in a dorsiflexion position at times or a normal position at other times.

The present disclosure includes a device for treating ankle equinus by stretching the Gastrocnemius muscle and soleus muscle, the device comprising a brace comprising an elongated rod, an adjustable slider, a clamp and a footplate, wherein the elongated rod includes at least one tab for fixing an angle of dorsiflexion for an ankle of a user; wherein the footplate includes a bottom plate, at least one side plate having at least one opening for attachment to the at least one tab, and an ankle hinge; an adjustable slider configured to be attached adjacent to the elongated rod above the heel, wherein the adjustable slider extends vertically to change the overall length of the device to accommodate different leg lengths of different users; and a toe wedge supported by the footplate, wherein the brace locks the knee in extension while also locking the ankle of a user in a dorsiflexion position at times or a normal position at other times.

The present disclosure includes a device for treating ankle equinus by stretching the Gastrocnemius muscle and soleus muscle, the device comprising a brace comprising an elongated rod, an adjustable slider, a clamp and a footplate, wherein the elongated rod includes a left sidewall and a right sidewall configured to attach to the footplate, and a plurality of side webbing slots, wherein the left and right sidewalls each include at least one tab for fixing an angle of dorsiflexion for an ankle of a user; wherein the footplate includes a bottom plate, a left side plate and a right side plate with each side plate having at least one opening for attachment to the at least one tab of the left and right sidewalls of the elongated rod through the side plates, an ankle hinge, and a plurality of foot webbing slots; wherein the ankle hinge of the elongated rod and the foot plate creates an opening for the heel of a user; the adjustable slider configured to be attached adjacent to the elongated rod above the heel, the adjustable slider defining a center slot extending along a substantial length of the slider, wherein the adjustable slider extends vertically to change the overall length of the device to accommodate different leg lengths of different users; and the clamp configured for connecting the adjustable slider and the elongated rod; and a wedge supported by the footplate, wherein the brace locks the knee in extension while also locking the ankle of a user in a dorsiflexion position at times or a normal position at other times.

In one embodiment of the invention, the brace further comprises a knee pad for the knee of a user during placement in the brace. Additionally, the brace may further comprise a foot pad for the top of a user's foot while placed in the brace.

The device may also further comprise a plurality of webbing straps configured to insert into the side webbing slots.

In another embodiment, the elongated rod is capable of being attached to the foot plate by at least one screw.

In another embodiment of the invention, the device may further comprising a wedge supported by the footplate. The wedge may be located beneath the hallux of the user and may be configured to engage the user's Windlass Mechanism.

In another embodiment of the invention, the footplate includes a negative heel rocker sole. In this embodiment, the negative heel rocker sole may have a degree angle to match an angle of dorsiflexion of the ankle when the ankle is in a dorsiflexion position. In particular, the negative heel rocker sole has a degree angle selected from the group consisting of 5, 10, and 15 degrees.

In one embodiment of the method, the brace has a goniometer, and the method further comprises the step of measuring the angle of the ankle of the user using the brace.

From the present disclosure, the equinus is associated with any condition selected from the group consisting of Heel Spur Syndrome, Plantar fasciitis, Neuromuscular disorders including disorders selected from the group consisting of Cerebral Palsy and Friedreich's Ataxia, Congenital disorders including disorders selected from the group consisting of Congenital equinus, Clubfoot, Vertical Talus and Calcaneal Valgus, Pediatric Flexible Flatfoot deformity, Adult Flexible Flatfoot deformity, Tibialis Posterior Tendon Dysfunction, Achilles tendonitis, Achilles tendon injuries, Haglund's Deformity, Retrocalcaneal heel spurs and tendonosis, Tarsal Coalitions, Bunion deformities, Metatarsalgia, Forefoot pain, Charcot deformity, Diabetic forefoot ulcers and toe ulcers, Equinovarus deformities from post-injury or post-stroke patients, Post Transmetatarsal or Chopart's amputation patients, Midfoot degenerative joint disease at Lis Franc's joint or Chopart's joint, Hypermobile first ray disorders and Cross-over toe deformities.

DETAILED DESCRIPTION

For the purpose of promoting an understanding of the principles of the invention, reference will now be made to certain embodiments illustrated in the disclosure, and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
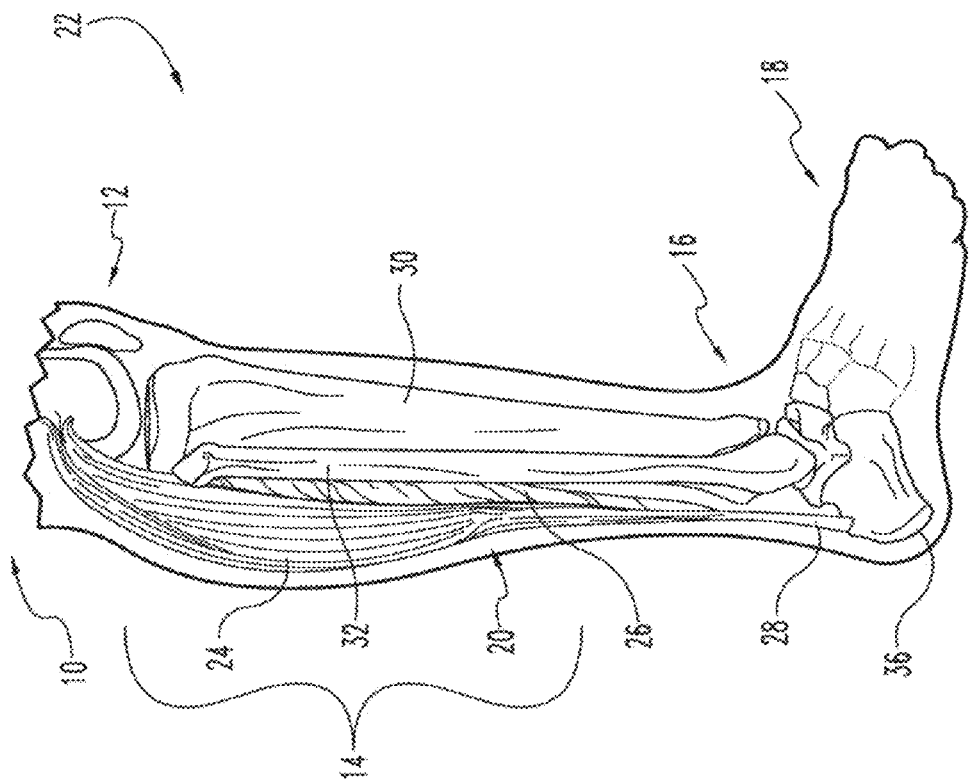
FIG. 1 is a back view of calf muscles with a knee at extension and an ankle at neutral position.
Figure 2:
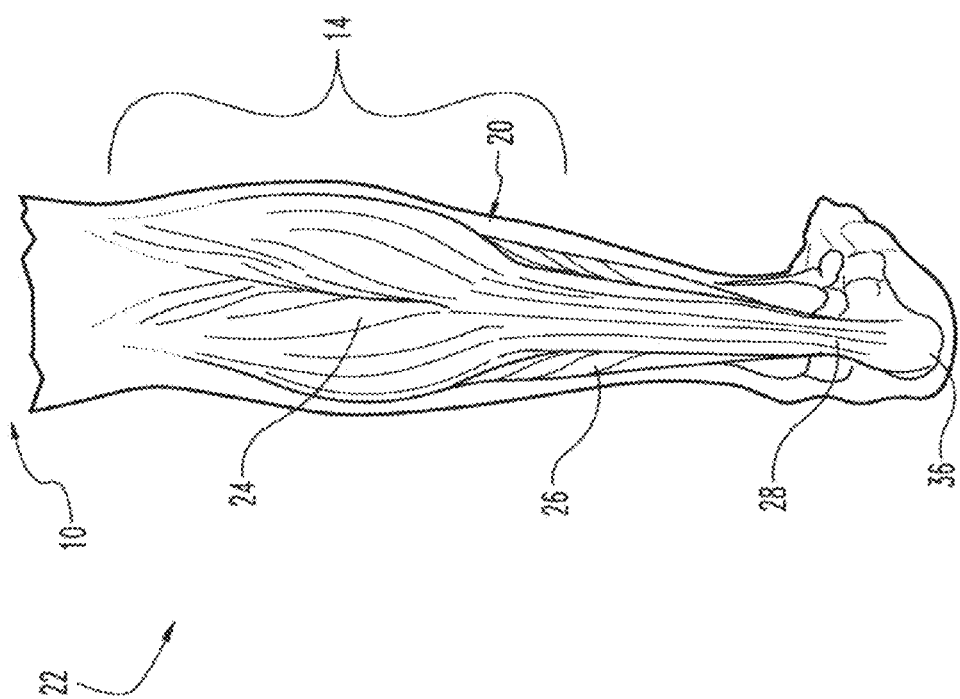
FIG. 2 is a side view of the calf muscles of FIG. 1.

As shown in FIGS. 1 and 2, thigh 10, knee 12, calf 14, ankle 16, foot 18, and calf muscles 20 of user 22 are illustrated. Calf muscles 20 are shown as gastrocnemius muscle 24 and soleus muscle 26. Each of these muscles 24, 26 shares a common insertion (attachment) via Achilles tendon 28 into the posterior calcaneus. Soleus muscle 26 originates at the proximal to medial portions of tibia 30 and fibula 32. Soleus muscle 26 and gastrocnemius muscle 24 unite via their respective apponeurosis to form Achilles tendon 28. Unlike soleus muscle 26, gastrocnemius muscle 24 originates at posterior femur 34 just above knee 12 and also inserts into heel 36. Gastrocnemius muscle 24 crosses two joints: knee 12 and ankle 16.

As illustrated with knee 12 in extension and ankle 16 in normal position, soleus muscle 26 and gastrocnemius muscle 24 are not stretched to capacity in a person with normal ankle range of motion including maximum ankle dorsiflexion of twenty-five degrees (25°). In a person with limited ankle range of motion, such as equinus, soleus muscle 26 or gastrocnemius muscle 24 may be stretched to capacity with knee 12 in extension for gastroc equinus or gastrosoleal equinus and ankle 16 in normal position or in a dorsiflexed position.

Figure 3:
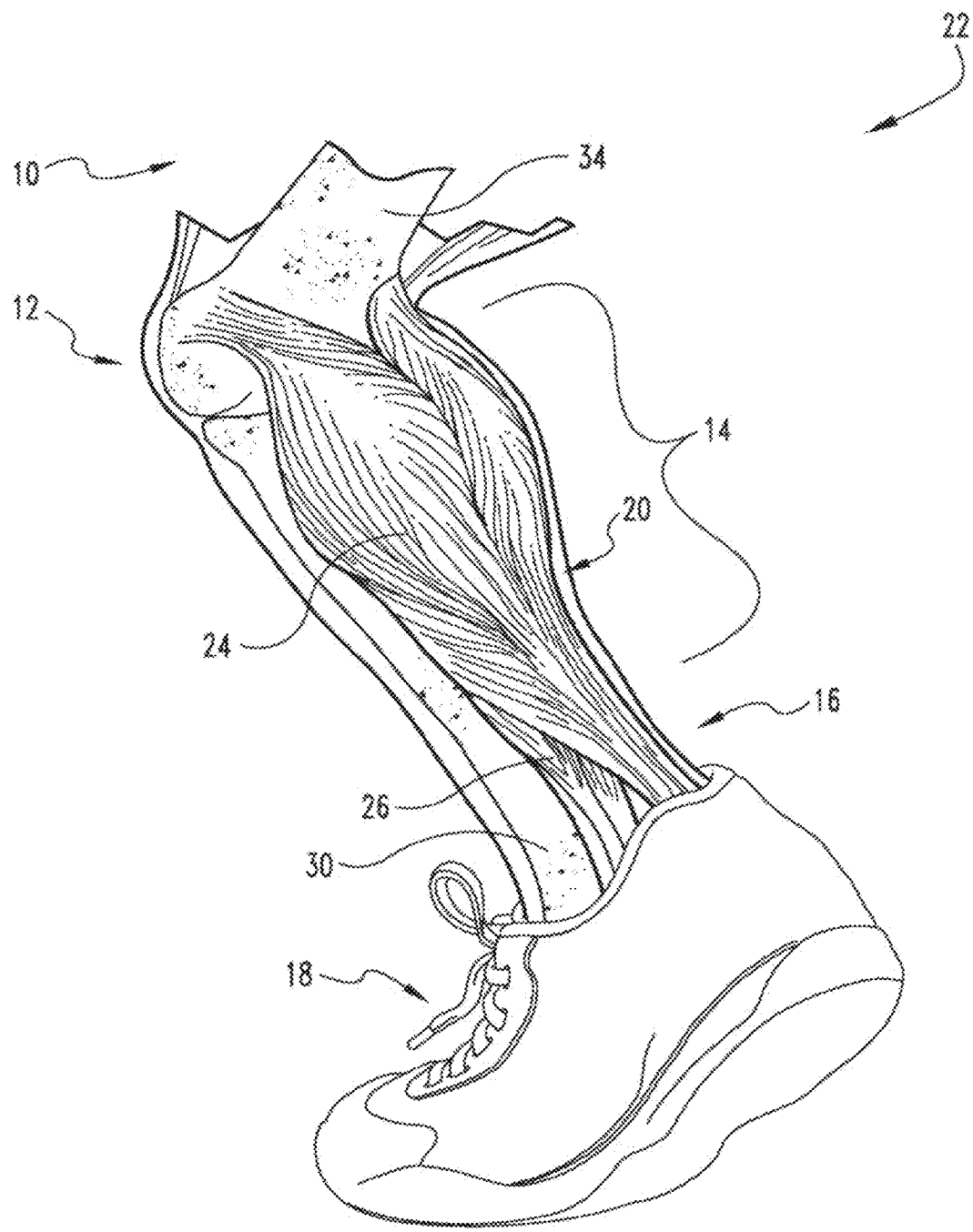
FIG. 3 is a perspective view of calf muscles with a knee in flexion and the ankle in dorsiflexion.

As illustrated in FIG. 3, a person with limited ankle range of motion due to gastroc equinus, moving knee 12 from extension to flexion releases gastrocnemius muscle 24 from full stretch capacity. A person suffering from gastroc equinus may be able to place ankle 16 in dorsiflexion with knee 12 in flexion even though gastrocnemius muscle 24 is shortened.

Figure 4:
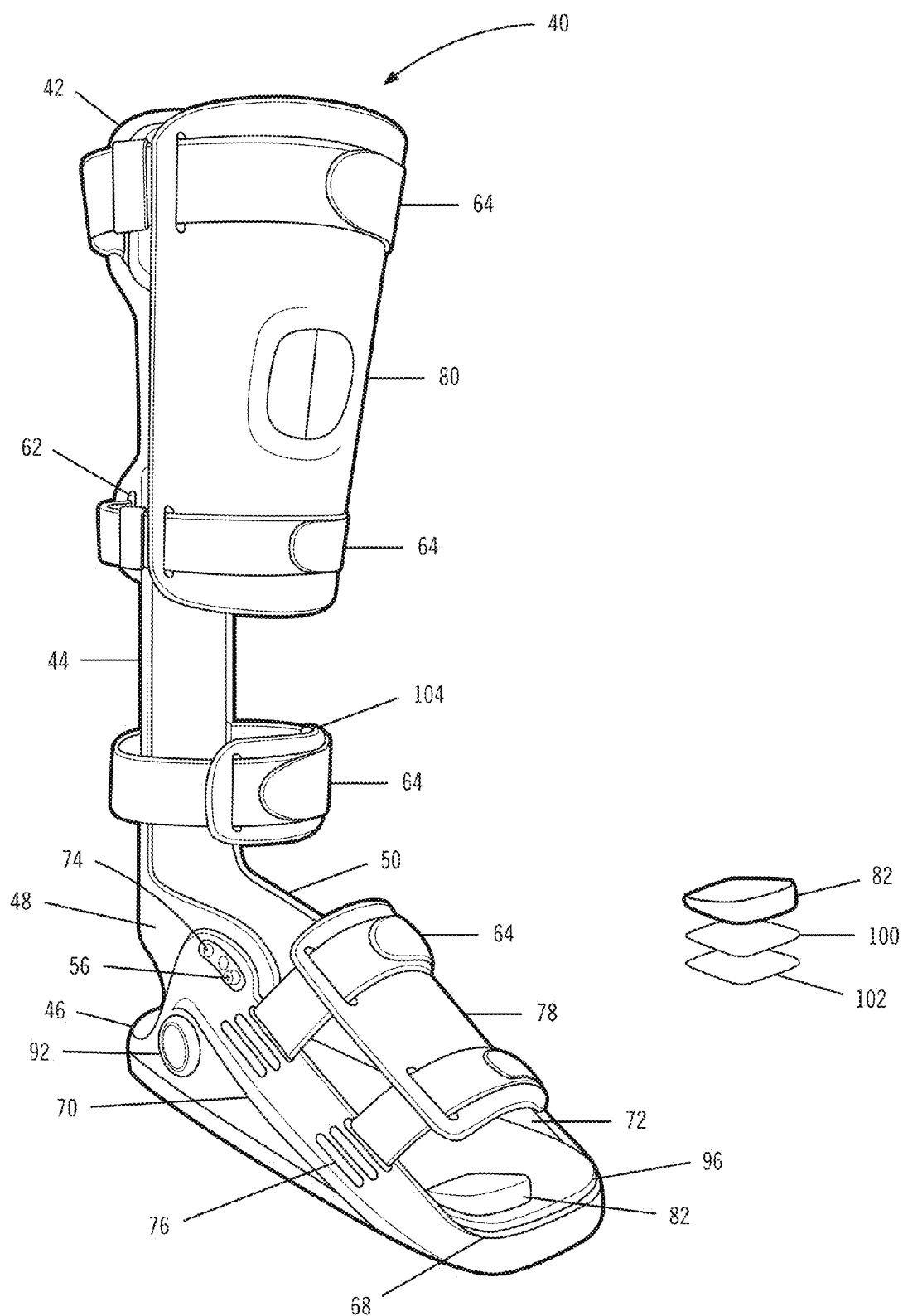
FIG. 4 is a stylized perspective view of a brace/device according to an embodiment of the present disclosure.

Device 40 according to an embodiment of the present disclosure is illustrated in FIG. 4. Device 40 is a brace configured for full extension of knee 12 while optionally while dorsiflexing ankle 16. Each part included in device 40 can be manufactured from materials known in the industry for durability and ease, including plastic molded shell, metal, vinyl, rubber, or wood. In a particular embodiment, device 40 is constructed of plastic molded shell.

Figure 5:
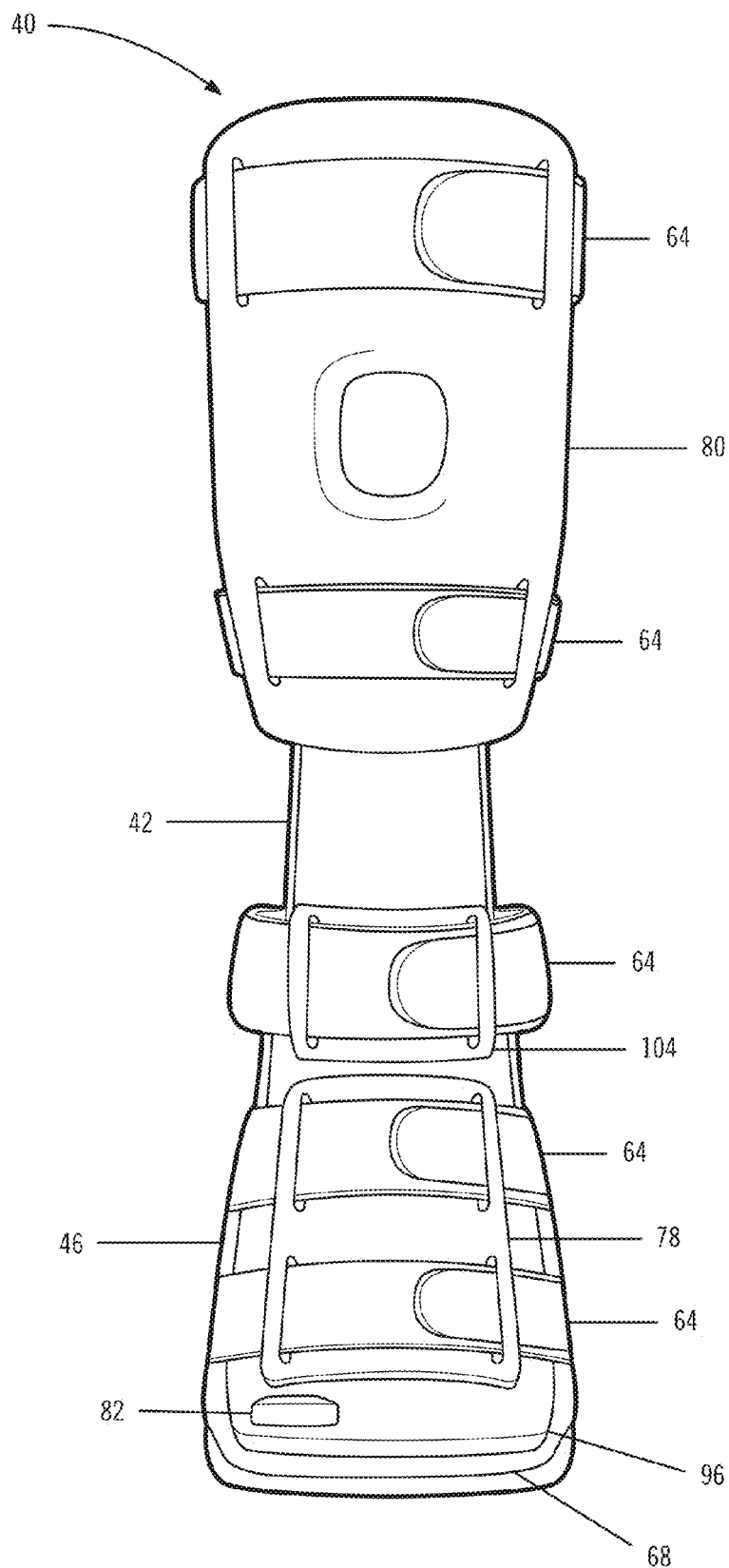
FIG. 5 is a front view of the brace of FIG. 4.
Figure 6:
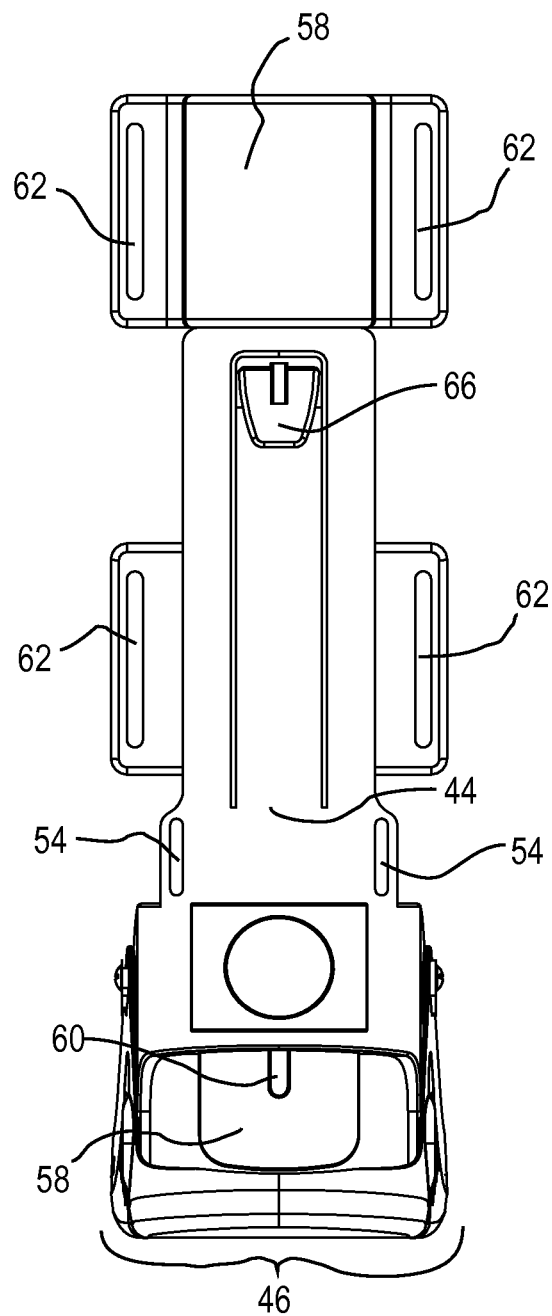
FIG. 6 is a back view of a reduced brace according to another embodiment of the present disclosure.

As shown in FIGS. 4-6, device 40 includes base 42 comprising elongated rod 44 and footplate 46. Elongated rod 44 is configured to extend along the posterior of lower thigh 10 of the leg of a user from above knee 12 to the top of heel 36. Elongated rod 44 is generally rectangular in shape, but can be easily configured in other geometric shapes to fit the leg of a user. Base 42 also optionally includes left sidewall 48 and right sidewall 50 configured to attach to footplate 46. Left and right sidewalls 48, 50 may be machined into different shapes configured to surround the sides of foot 18. Each sidewall 48, 50 also includes tab 56 which is configured to insert into opening 74 of footplate 46. Tab 56 can be used to set the angle of dorsiflexion of ankle 16 of user 22. In one embodiment of the present disclosure, openings 74 are positioned to correspond to 0°, 10°, and 20° of ankle dorsiflexion. Tab 56 can be of varying shapes to correspond to opening 74 on footplate 46 and can reversibly mate with opening 74 by standard fastening methods, including by a lock-and-key combination or by snug fit. This allows for tool-less installation and assembly, if necessary, as well as ease of shipping and packaging. In one embodiment, tab 56 is cylindrical. In another embodiment, a screw may be utilized either instead of or complementary to tab 56 for tooled assembly. Each sidewall also optionally includes at least one ankle hinge opening 94 configured to support at least one ankle hinge 92.

Figure 11:
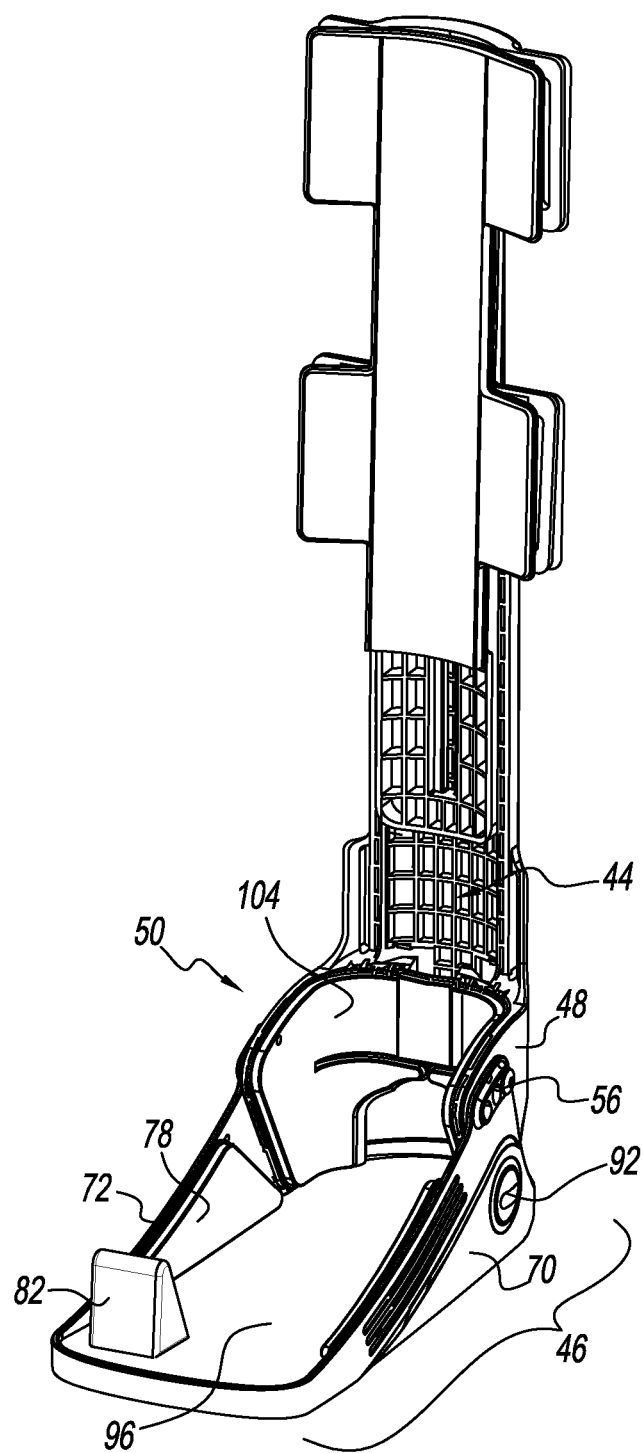
FIG. 11 is a front perspective view of the brace of FIG. 6 with the adjustable slider in an extended position.
Figure 12:
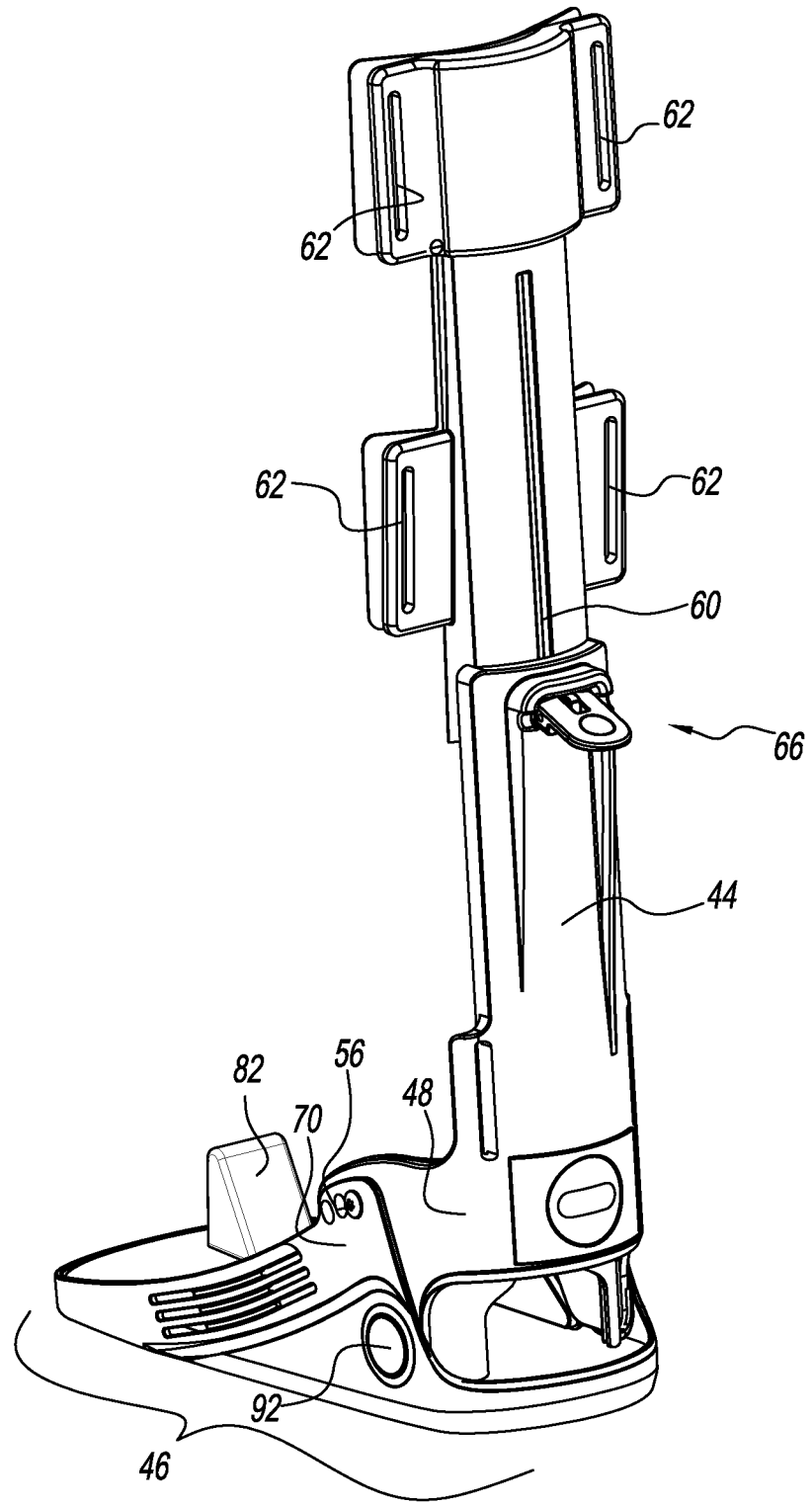
FIG. 12 is a back perspective view of the brace of FIG. 6 with the adjustable slider in an extended position.

In one embodiment, adjustable slider 58 defines slider center slot 60. Center slot 60 is configured to extend a significant portion of the length of slider 58 in order to maximize length adjustment of brace 40 (see FIGS. 11 and 12). In an alternative embodiment, elongated rod 44 alternatively defines center slot 52. In yet another alternative embodiment, both elongated rod 44 and adjustable slider 58 define slots to maximize length adjustment of brace 40.

Center slot 60 is configured to allow clamp 66 to pass through slot 60 for locking and unlocking of adjustable slider 58 and elongated rod 44. Unlocking clamp 66 allows for adjustment of the length of brace 42 based upon the needs of user 22.

Elongated rod 44 may also optionally have a plurality of side webbing slots 54 for insertion of adjustable straps 64 to fix device 40 to thigh 10, knee 12, calf 14 and ankle 16 of a user as shown in FIG. 4. Side webbing slots 54 can be of varying lengths and dimensions according to the width and thickness of the webbing.

Device 40 may also include adjustable straps 64 with optional foot padding 78, knee padding 80, and ankle padding 104. Adjustable straps 64 and padding 78, 80 extend about 4-6 cm anterior and posterior above knee 12 of user 22. Additional adjustable straps 64 with pads 78, 80 anterior and posterior to the tibia 30 and calf 14 extending from the tibial tubercle to the inferior border of the calf 14 of user 22 are also envisioned. The webbing material for adjustable straps 64 can be of a generalized material known in the industry, including cord, nylon, cotton, polypropylene, vinyl, and elastic.

Figure 10:
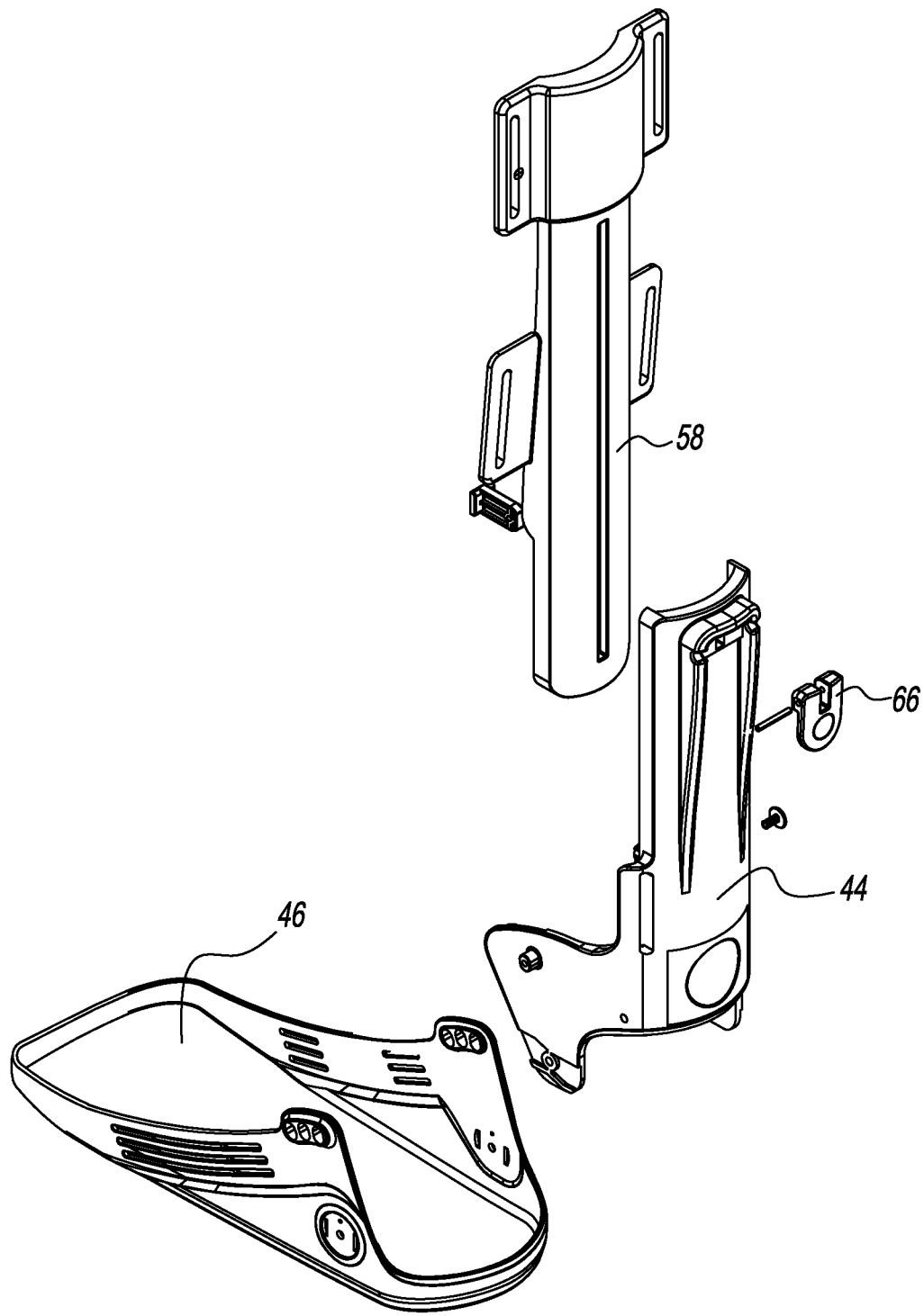
FIG. 10 is an exploded view of the adjustable slider, the elongated rod, the clamp, and the footplate of the brace of FIG. 6.

Adjustable slider 58 of device 40, as shown in FIG. 10, is configured to attach adjacently to elongated rod 44 above heel 36 (see FIG. 10). This can be done by slidable attachment or by use of clamp 66 to lock adjustable slider 58 against elongated rod 44. Adjustable slider 58 is sized and shaped to correspond to elongated rod 44. Adjustable slider 58 also has center slot 60 and side webbing slots 62. In one embodiment, center slot 60 and side slots 62 correspond in size and placement to center slot 52 and optional side webbing slots 54 of elongated rod 44. In another embodiment, center slot 60 corresponds in size and placement to the center area etched into elongated rod 44. Adjustable slider 58 extends vertically to change the overall length of device 40 to accommodate different leg lengths of different users 22 (see FIGS. 11 and 12).

Clamp 66 is used to lock adjustable slider 58 against elongated rod 44. Adjustable slider 58 extends vertically to change the overall length of device 40 to accommodate different leg lengths of different users 22. As shown in FIG. 6, clamp 66 is attached on the exterior surface of elongated rod 44 and is configured for connecting to adjustable slider 58.

Figure 7:
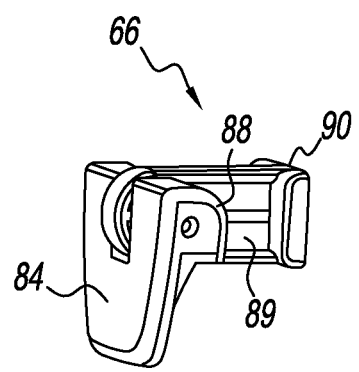
FIG. 7 is a perspective view of the clamp of FIG. 6.

As illustrated in FIG. 7, clamp 66 includes clip 84 including camshaft projection 88. Clamp 66 also includes spacer 89 and abutment 90. In operation, rotation of clip 84 from a vertical orientation to a horizontal orientation, increases space between camshaft projection 88 and abutment 90. The increased space is sufficient to allow adjustable slider 58 to extend relative to elongated rod 44. Rotation of clip 84 from a horizontal orientation to a vertical orientation, decreases space between clip 84 and abutment 90, locking adjustable slider 58 relative to elongated rod 44.

In one embodiment, camshaft protection 88 and abutment 90 of clamp 66 pass through center slots 52, 60 to reversibly lock adjustable slider 58 to elongated rod 44. When clamp 66 is in a locked position, adjustable slider 58 is unable to extend to accommodate different leg lengths of user 22. When clamp 66 is in an unlocked position, adjustable slider 58 can be repositioned vertically to a user's individual leg length. In another embodiment, camshaft protection 88 and abutment 90 of clamp 66 are machined into elongated rod 44 of base 42 to reversibly lock and unlock adjustable slider 58 to elongated rod 44.

Figure 8:
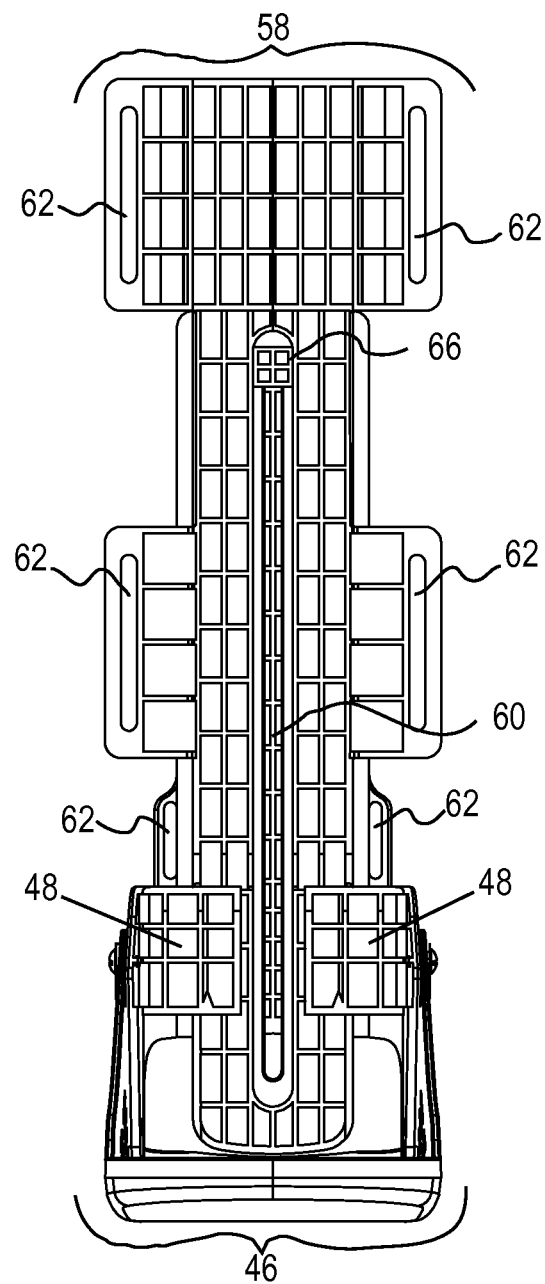
FIG. 8 is a front view of the base and the retracted adjustable slider of FIG. 6.

As best illustrated in FIG. 8, footplate 46 includes bottom plate 68, left side plate 70 and right side plate 72 with each side plate having at least one opening 74 for attachment to the at least one tab 56 of the left and right sidewalls 48, 50 of elongated rod 44 through left and right side plates 70, 72, ankle hinge 92, and a plurality of foot webbing slots 76, sole 96, and optional toe wedge 82. Footplate 46 attaches to elongated rod 44 at the at least one tab 56 and at ankle hinge 92 and creates an opening to expose heel 36 of user 22.

Bottom plate 68 of footplate 46 is configured for the bottom of the foot 18 of user 22. It can be covered with sole 96. Sole 96 is removably coupled to bottom plate 68 of footplate 46 and includes tread pattern 61 to prevent slippage.

Footplate 46 also includes a left side plate 70 and right side plate 72 for supporting foot 18, ankle 16 and heel 36 of user 22. Side plates 70, 72 are contoured for aesthetic value and for air flow through footplate 46 and corresponding with the size and shaping of the left and right sidewalls 48, 50 of elongated rod 44 for further support surrounding foot 18 of user 22. Each side plate has at least one opening 74 for attachment to at least one tab 56 of left and right sidewalls 48, 50 of elongated rod 44. Opening 74 is configured to correspond with the shape of tab 56, which can be configured with any standard geometric shapes. In one embodiment, opening 74 is circular. Attachment of tab 56 to opening 74 is reversible and rotatable when tab 56 is cylindrical.

Ankle hinge 92 connects footplate 46 to elongated rod 44. Ankle hinge 92 is configured to be located adjacent to the ankle of user 22. Ankle hinge 92 allows for plantarflexion and dorsiflexion of the ankle of user 22. Ankle hinge 92 in conjunction with tabs 56 and openings 74 allow for precise control of ankle position of user 22. In another embodiment ankle hinge 92 also includes a locking feature which allows user's ankle to be locked in any position, such as normal, plantarflexion or dorsiflexion. In combination with other components of device 40, ankle hinge 92 aids in stretching user's gastrocnemius and soleus muscles. Specifically, ankle hinge 92 allows for locking user's ankle in dorsiflexion while elongated rod 44 and adjustable slider 58 allow for locking user's knee in extension. The combination of knee in extension and ankle in dorsiflexion aids in full stretching of the gastrocnemius and soleus muscles of user 22.

Device 40 with multiaxial ankle hinges 92 may be useful to provide ankle dorsiflexion of user 22 and correction of forefoot varus, forefoot valgus, rearfoot varus, or rearfoot valgus.

Footplate 46 also includes a plurality of foot webbing slots 76 for insertion of adjustable straps 64 to fix device 40 to foot 18 of user 22. Foot webbing slots 76, as akin to side webbing slots 54, can be of varying lengths and dimensions according to the width and thickness of the webbing.

Toe wedge 82, as shown in FIGS. 4, 5, 8, and 9 is optionally included with footplate 46. Toe wedge 82 is configured to be fixed at a location beneath the hallux of user 22. Hook and loop mechanism 100, 102 fixes toe wedge 82 to footplate 46. Hook 100 and loop 102 are interchangeable. As an example, hook 100 is configured to be attached to footplate 46 and loop 102 is configured to be attached to hook 100. Loop 102 also includes adhesive to attach to padding of sole 96. Toe wedge 82 is configured to engage user's Windlass Mechanism, which dorsiflexes the hallux (i.e., big toe) of foot 18 to tighten the plantar fascia thereby supinating the hindfoot (i.e., talus and calcaeneus). As muscles 24, 26 share a common insertion (attachment) via Achilles tendon 28 into the posterior calcaneus, activation of user's Windlass Mechanism further stretches the muscles 24, 26. Multiple toe wedges 82 are available at varying angles. For example, toe wedges 82 may have any degree from thirty degree (30°) to ninety degree (90°) angles. In on embodiment, toe wedge 82 has an angle of 60°. Additional toe wedge angles are envisioned. Alternatives for engaging the Windlass Mechanism are envisioned. For example, a loop of material may raise the hallux in order to engage the Windlass Mechanism.

Figure 9:
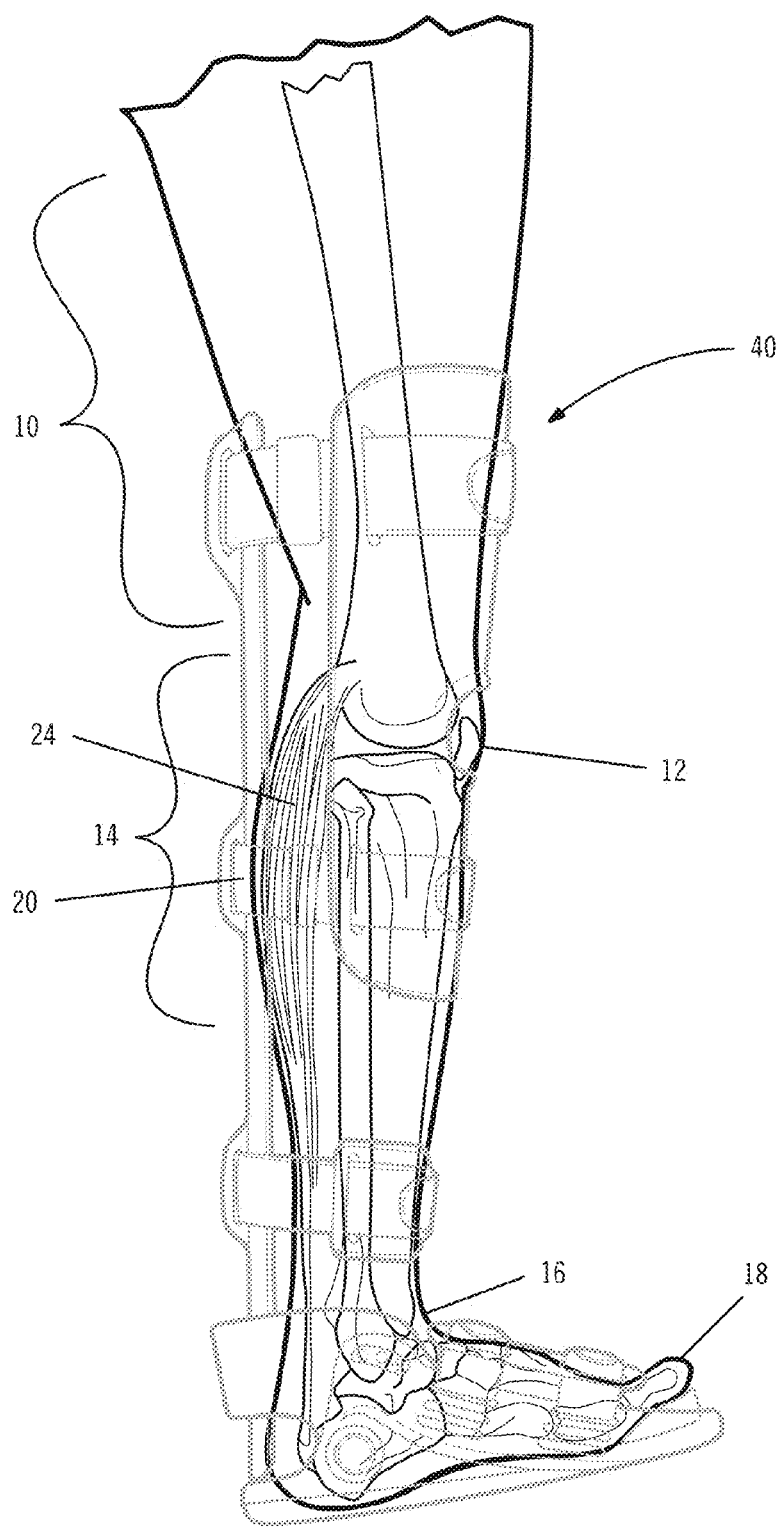
FIG. 9 is a side view of the brace of FIG. 6 and calf muscles with a knee at extension and an ankle in dorsiflexion.

As shown in FIGS. 4, 5 and 9, knee padding 80, ankle padding 104, and foot padding 78 may be optionally included in device 40 and configured with additional side and foot webbing slots 54, 76 for insertion of adjustable straps 64 though the padding for support of the knee 12, ankle 16 and top of the foot 18 of user 22. Padding 78, 80, 104 minimizes marking of the skin by rubbing and friction of straps 64 during use of the device and increases general comfortability to the user.

It is envisioned that device 40 can be used on either leg of user 22. Device 40 locks the knee in extension while also locking the ankle of a user in a dorsiflexion position at times or a plantarflexion position at other times.

FIG. 9 illustrates device 40 in use by user 22. Device 40 is effective in treating equinus. Device 40 is also effective in treating equinus associated with any of the following other conditions: Heel Spur Syndrome/Plantar fasciitis; neuromuscular disorders such as Cerebral Palsy and Friedreich's Ataxia; congenital disorders such as Congenital Equinus, Clubfoot, Vertical Talus, and, Calcaneal Valgus; Pediatric Flexible Flatfoot deformity; Adult Flexible Flatfoot deformity; Tibialis Posterior Tendon Dysfunction; Achilles tendonitis; Achilles tendon injuries; Haglund's Deformity; Retrocalcaneal heel spurs and tendonosis; Tarsal Coalitions; Bunion deformities; Metatarsalgia; Forefoot pain; Charcot deformity; Diabetic forefoot ulcers and toe ulcers; Equinovarus deformities from post-injury or post-stroke patients; Post Transmetatarsal or Chopart's amputation patients; Midfoot degenerative joint disease at Lis Franc's joint or Chopart's joint; Hypermobile first ray disorders and Cross-over toe deformities.

FIG. 9 is also useful in illustrating methods of treating equinus by stretching user's gastrocnemius muscle. The following illustrated steps of treating equinus using device 40 are: (a) locking knee 12 of user 22 in extension, (b) locking ankle 16 of user 22 in dorsiflexion using ankle hinge 92 of device 40, thereby stretching user's gastrocnemius muscle 24 and soleus muscle 26.

Because device 40 is a targeted stretch of gastrocnemius muscle 24 and soleus muscle 26, device 40 may be used for a shorter period of time than a traditional night splint. Device 40 may yield quicker and more effective results in correction of equinus. Device 40 may provide the same benefit of a traditional night splint without user 22 having to wear device 40 overnight. For example, device 40 worn for two 30 minute sessions per day may provide the same benefit of a traditional night splint worn overnight. This example is based on a meta-analysis by Radford et al. in the British Journal of Sports Medicine 2006. In comparison to a traditional night splint, device 40 may not need to be worn overnight, improving user compliance and providing user with a more comfortable and restful sleep.

Device 40 may be used for a shorter treatment period than other devices. For example, device 40 may be used for one (1) to three (3) months. Some users, especially athletic participants and children, may benefit from a maintenance program after treatment. The maintenance program may involve use of device 40 on a less regular schedule for a period of time to maintain the desired correction.

Device 40 may come with written or digital instructions for users, physicians and therapists. Device 40 may be packaged with Frequently Asked Questions or links to websites for additional information, such as instructions on use.

While the inventions have been illustrated and described in detail in the drawings and foregoing description, the same is to be considered as illustrative and not restrictive in character, it being understood that the preferred embodiment has been shown and described and that changes and modifications that come within the spirit of the invention are desired to be protected.

What is claimed is:

1. A device for treating ankle equinus by stretching the Gastrocnemius muscle and soleus muscle, the device comprising:
   a brace comprising an elongated rod, an adjustable slider, a clamp and a footplate,
   wherein the elongated rod includes a left sidewall and a right sidewall configured to attach to the footplate, and a plurality of side webbing slots,
   wherein the left and right sidewalls each include at least one tab for fixing an angle of dorsiflexion for an ankle of a user;
   wherein the footplate includes a bottom plate, a left side plate and a right side plate with each side plate having at least one opening for attachment to the at least one tab of the left and right sidewalls of the elongated rod through the side plates, an ankle hinge, and a plurality of foot webbing slots;
   wherein the ankle hinge of the elongated rod and the foot plate creates an opening for the heel of a user;

the adjustable slider configured to be attached adjacent to the elongated rod above the heel, the adjustable slider defining a center slot extending along a substantial length of the slider, wherein the adjustable slider extends vertically to change the overall length of the device to accommodate different leg lengths of different users;

the clamp configured for connecting the adjustable slider and the elongated rod; and a wedge supported by the footplate, wherein the brace locks the knee in extension while also locking the ankle of a user in a dorsiflexion position at times or a normal position at other times.

2. The device of claim 1 wherein the center slot is configured to allow the clamp to pass through for locking and unlocking the adjustable slider to the elongated rod.

3. The device of claim 1 wherein the clamp includes a clip, a spacer, and an abutment, and the spacer is configured to pass through the center slot and lock or unlock the adjustable slider to the elongated rod.

4. The device of claim 3 wherein the clip includes a camshaft projection.

5. The device of claim 4 wherein the clip in horizontal orientation does not engage the camshaft projection, providing enough space to allow for free movement between the elongated rod and the adjustable slider.

6. The device of claim 4 wherein the clip in vertical orientation engages the camshaft projection, locking the elongated rod and the adjustable slider relative to each other.

7. A device for treating ankle equinus by stretching the Gastrocnemius muscle and soleus muscle, the device comprising:

a brace comprising an elongated rod, an adjustable slider, a clamp and a footplate, wherein the elongated rod includes at least one tab for fixing an angle of dorsiflexion for an ankle of a user;

wherein the footplate includes a bottom plate, at least one side plate having at least one opening for attachment to the at least one tab, and an ankle hinge;

an adjustable slider configured to be attached adjacent to the elongated rod above the heel, wherein the adjustable slider extends vertically to change the overall length of the device to accommodate different leg lengths of different users; and a toe wedge supported by the footplate, wherein the brace locks the knee in extension while also locking the ankle of a user in a dorsiflexion position at times or a normal position at other times.

8. The device of claim 7, wherein the wedge is located beneath the hallux of the user.

9. The device of claim 7, wherein the wedge is configured to engage the user's Windlass Mechanism.

10. The device of claim 7, wherein the wedge has any angle within the range of approximately thirty degrees to approximately ninety degrees.

11. The device of claim 10, wherein the wedge has an angle of 60°.

12. A device for treating ankle equinus by stretching the Gastrocnemius muscle and soleus muscle, the device comprising:

a brace comprising an elongated rod, an adjustable slider, a clamp and a footplate, wherein the elongated rod includes a left sidewall and a right sidewall configured to attach to the footplate, and a plurality of side webbing slots, wherein the left and right sidewalls each include at least one tab for fixing an angle of dorsiflexion for an ankle of a user;

wherein the footplate includes a bottom plate, a left side plate and a right side plate with each side plate having at least one opening for attachment to the at least one tab of the left and right sidewalls of the elongated rod through the side plates, an ankle hinge, and a plurality of foot webbing slots;

wherein the ankle hinge of the elongated rod and the foot plate creates an opening for the heel of a user;

the adjustable slider configured to be attached adjacent to the elongated rod above the heel, the adjustable slider defining a center slot extending along a substantial length of the slider, wherein the adjustable slider extends vertically to change the overall length of the device to accommodate different leg lengths of different users;

the clamp configured for connecting the adjustable slider and the elongated rod; and a wedge supported by the footplate, wherein the brace locks the knee in extension while also locking the ankle of a user in a dorsiflexion position at times or a normal position at other times.

13. The device of claim 12, wherein the at least one opening is positioned to correspond to any angle within the range of approximately zero degrees to approximately twenty degrees of ankle dorsiflexion.

14. The device of claim 13 wherein the at least one opening includes at least three openings.

15. The device of claim 14 wherein the at least three openings correspond to 0°, 10°, and 20° of ankle dorsiflexion.

16. The device of claim 12, wherein the equinus is associated with any condition selected from the group consisting of:

a. Heel Spur Syndrome, Plantar fasciitis
b. Neuromuscular disorders including disorders selected from the group consisting of Cerebral Palsy and Friedreich's Ataxia
c. Congenital disorders including disorders selected from the group consisting of Congenital equinus, Clubfoot, Vertical Talus and Calcaneal Valgus
d. Pediatric Flexible Flatfoot deformity
e. Adult Flexible Flatfoot deformity
f. Tibialis Posterior Tendon Dysfunction
g. Achilles tendonitis
h. Achilles tendon injuries
i. Haglund's Deformity
j. Retrocalcaneal heel spurs and tendonosis
k. Tarsal Coalitions
l. Bunion deformities
m. Metatarsalgia
n. Forefoot pain
o. Charcot deformity
p. Diabetic forefoot ulcers and toe ulcers
q. Equinovarus deformities from post-injury or post-stroke patients
r. Post Transmetatarsal or Chopart's amputation patients
s. Midfoot degenerative joint disease at Lis Franc's joint or Chopart's joint
t. Hypermobile first ray disorders and
u. Cross-over toe deformities.

* * * * *